(12) United States Patent
Wang et al.

(10) Patent No.: US 9,381,335 B2
(45) Date of Patent: Jul. 5, 2016

(54) BLADDER WALL DRUG DELIVERY SYSTEM

(71) Applicant: AMS Research Corporation, Minnetonka, MN (US)

(72) Inventors: Guangjian Wang, Falcon Heights, MN (US); Brian P. Watschke, Minneapolis, MN (US)

(*) Notice: Subject to any disclaimer, the term of this patent is extended or adjusted under 35 U.S.C. 154(b) by 0 days.

(21) Appl. No.: 13/793,248

(22) Filed: Mar. 11, 2013

(65) Prior Publication Data

US 2013/0253477 A1  Sep. 26, 2013

Related U.S. Application Data

(60) Provisional application No. 61/613,744, filed on Mar. 21, 2012.

(51) Int. Cl.
| | | |
|---|---|---|
| *A61M 31/00* | (2006.01) | |
| *A61M 25/00* | (2006.01) | |
| *A61M 25/01* | (2006.01) | |
| *A61B 5/00* | (2006.01) | |
| *A61B 1/04* | (2006.01) | |

(52) U.S. Cl.
CPC .............. *A61M 31/00* (2013.01); *A61B 1/043* (2013.01); *A61B 5/0084* (2013.01); *A61M 2025/0008* (2013.01); *A61M 2025/0166* (2013.01)

(58) Field of Classification Search
CPC .......... A61M 25/0017; A61M 31/002; A61M 2025/0008; A61M 2210/1085; A61B 5/0084; A61B 1/307; A61B 18/24
USPC .......... 604/517, 275, 279, 264, 508, 523, 544
See application file for complete search history.

(56) References Cited

U.S. PATENT DOCUMENTS

| | | |
|---|---|---|
| 4,701,162 A | 10/1987 | Rosenberg |
| 4,705,502 A | 11/1987 | Patel |
| 4,792,330 A | 12/1988 | Lazarus et al. |
| 4,848,367 A | 7/1989 | Avant et al. |
| 4,873,977 A | 10/1989 | Avant et al. |
| 4,909,785 A | 3/1990 | Burton et al. |
| 4,911,164 A | 3/1990 | Roth |
| 4,932,956 A | 6/1990 | Reddy et al. |
| 5,047,039 A | 9/1991 | Avant et al. |
| 5,123,908 A | 6/1992 | Chen |
| 5,152,772 A | 10/1992 | Sewell, Jr. |
| 5,540,701 A | 7/1996 | Sharkey et al. |
| 5,545,171 A | 8/1996 | Sharkey et al. |
| 5,695,504 A | 12/1997 | Gifford, III et al. |

(Continued)

FOREIGN PATENT DOCUMENTS

| | | |
|---|---|---|
| WO | WO 92/04869 | 4/1992 |
| WO | WO 96/07447 | 3/1996 |

(Continued)

*Primary Examiner* — Rebecca E Eisenberg
(74) *Attorney, Agent, or Firm* — Kagan Binder, PLLC

(57) ABSTRACT

A catheter based drug delivery system for minimally invasive delivery of treatment drugs into a bladder wall. The catheter system can include a delivery tip for deforming the bladder wall before forming jets of drug solution that penetrate the bladder wall for needleless delivery of the treatment drugs directly to the diseased tissue. The delivery tip can also have graduated markings for providing visual indicators of the relative depth of the delivery tip in the bladder wall and the alignment of the formed jets with the particular layers of the bladder wall.

23 Claims, 3 Drawing Sheets

(56) References Cited

U.S. PATENT DOCUMENTS

| | | | |
|---|---|---|---|
| 5,707,380 A | 1/1998 | Hinchliffe et al. |
| 5,833,698 A | 11/1998 | Hinchliffe et al. |
| 5,931,842 A | 8/1999 | Goldsteen et al. |
| 5,964,791 A | 10/1999 | Bolmsjö |
| 6,024,748 A | 2/2000 | Manzo et al. |
| 6,119,045 A | 9/2000 | Bolmsjö |
| 6,149,667 A | 11/2000 | Hovland et al. |
| 6,193,734 B1 | 2/2001 | Bolduc et al. |
| 6,238,368 B1 | 5/2001 | Devonec |
| 6,254,570 B1 | 7/2001 | Rutner et al. |
| 6,299,598 B1 | 10/2001 | Bander |
| 6,302,905 B1 | 10/2001 | Goldsteen et al. |
| 6,391,039 B1 | 5/2002 | Nicholas et al. |
| 6,416,545 B1 | 7/2002 | Mikus et al. |
| 6,440,146 B2 | 8/2002 | Nicholas et al. |
| 6,447,533 B1 | 9/2002 | Adams |
| 6,461,367 B1 | 10/2002 | Kirsch et al. |
| 6,485,496 B1 | 11/2002 | Suyker et al. |
| 6,494,908 B1 | 12/2002 | Huxel et al. |
| 6,520,974 B2 | 2/2003 | Tanner et al. |
| 6,530,932 B1 | 3/2003 | Swayze et al. |
| 6,562,024 B2 | 5/2003 | Alvarez de Toledo et al. |
| 6,565,579 B2 | 5/2003 | Kirsch et al. |
| 6,602,243 B2 | 8/2003 | Noda |
| 6,695,832 B2 | 2/2004 | Schon et al. |
| 6,702,825 B2 | 3/2004 | Frazier et al. |
| 6,719,709 B2 | 4/2004 | Whalen et al. |
| 6,719,749 B1 | 4/2004 | Schweikert et al. |
| 6,726,697 B2 | 4/2004 | Nicholas et al. |
| 6,740,098 B2 | 5/2004 | Abrams et al. |
| 6,746,456 B2 | 6/2004 | Xiao |
| 6,746,472 B2 | 6/2004 | Frazier et al. |
| 7,549,424 B2 * | 6/2009 | Desai ............................ 128/898 |
| 8,439,867 B2 * | 5/2013 | Staskin .................... 604/103.01 |
| 2001/0049492 A1 | 12/2001 | Frazier et al. |
| 2002/0002363 A1 | 1/2002 | Urakawa et al. |
| 2002/0087176 A1 | 7/2002 | Greenhalgh |
| 2003/0069629 A1 | 4/2003 | Jadhav et al. |
| 2003/0208183 A1 | 11/2003 | Whalen et al. |
| 2003/0229364 A1 | 12/2003 | Seiba |
| 2004/0078047 A1 | 4/2004 | Nicholas et al. |
| 2004/0186538 A1 * | 9/2004 | Eshel ............................ 607/105 |

FOREIGN PATENT DOCUMENTS

| | | |
|---|---|---|
| WO | WO 99/16359 | 4/1999 |
| WO | WO 99/21490 | 5/1999 |
| WO | WO 99/21491 | 5/1999 |
| WO | WO 99/05808 | 11/1999 |
| WO | WO 2004/000135 | 12/2003 |
| WO | WO 2004/000136 | 12/2003 |
| WO | WO 2004/000137 | 12/2003 |
| WO | WO 2004/000138 | 12/2003 |
| WO | WO 2004/034913 | 4/2004 |

* cited by examiner

BLADDER WALL DRUG DELIVERY SYSTEM

RELATED APPLICATION

The present application claims the benefit of U.S. Provisional Application No. 61/613,744 filed Mar. 21, 2012, and entitled "BLADDER WALL DRUG DELIVERY SYSTEM", which is incorporated herein in its entirety by reference.

FIELD OF THE INVENTION

The present invention is directed to a catheter system for delivering drugs into a bladder wall. More specifically, the present invention is directed a catheter system with a delivery tip for delivering drugs into a bladder wall as a high pressure jet into a targeted location at predetermined depth within the bladder wall.

BACKGROUND OF THE INVENTION

The bladder is a hollow organ for receiving and storing urine before the urine is expelled from the body. The bladder typically comprises a multilayer wall including a mucus lining for resisting the corrosive effects of the urine and multiple muscle layers for contracting the bladder to expel the urine. Cancer and other disorders can form within the wall itself, either within an internal layer or between the layers, making treating the disorder difficult without invasive surgery. Similarly, the lining of the bladder can prevent treatment drugs administered within the bladder from penetrating deep enough into the wall to reach the diseased tissue. The disorders within the bladder wall can also make locating the treatment site itself difficult as the diseased tissue is often not readily visible from the interior or exterior of the wall.

One technique for treating disorders within the bladder wall is by navigating a catheter through the urethra into the interior of the bladder and dispensing the treatment drug proximately or topically to the bladder wall such that the treatment drug permeates into the wall to reach the diseased tissue. As the drugs must permeate through the outer layers of the wall to reach the diseased tissue, a highly concentrated solution or a large dosage must be administered to ensure that the treatment drug reaches the diseased tissue at a sufficient concentration to effectively treat the disorder. A similar drawback is that the treatment drugs can be dispersed over a large section of the bladder wall or diffuse into the healthy tissue surrounding the diseased tissue. In addition to wasting often expensive drugs on healthy tissue, the powerful drugs used for treating severely diseased tissue can also damage healthy tissue creating substantial complications.

Another technique includes incorporating a syringe or similar hollow tubed assembly into the catheter for penetrating the bladder wall and administering the treatment drugs directly into the diseased tissue within the bladder wall. Although this approach permits more accurate administration of the drug into the diseased tissue than permeation, estimating the depth of the syringe within the bladder wall can be difficult. As a result, the tip of the syringe can miss the diseased tissue resulting in ineffective drug delivery or puncture the bladder wall completely, thereby leading to serious complications. In addition, navigating the rigid needle or hollow tube through the urethra without damaging the side walls can be difficult.

As a result, there exists a need for additional techniques that treat diseased tissue within the bladder wall by accurately delivering treatment drugs into the bladder wall while minimizing the risk of complications from the procedure.

SUMMARY OF THE INVENTION

The present invention is directed to a drug delivery system for delivering a quantity of drugs to a predetermined location and depth within a bladder wall. The drug delivery system generally comprises a catheter with a delivery tip defining at least one orifice for forming a high pressure jet when a treatment drug solution is supplied to the delivery tip via the catheter. The delivery tip can be positioned against the bladder wall and oriented to direct the jets formed by the orifices into the diseased tissue within the bladder wall. The delivery tip can indent or penetrate the bladder wall to deform the bladder wall and align the formed jets with the desired tissue layer. The combination of the controlled bladder wall deformation and adjustment of the relative pressure and duration of the formed jets allows for targeted injection of the treatment drug and controlled dispersion of the treatment drug.

A drug delivery system according to one representative embodiment can comprise a catheter having a delivery tip defining at least one orifice. The catheter defines at least one lumen for supplying a treatment drug solution to the delivery tip at a variable pressure and duration. Each orifice is shaped to create a pressure jet of the delivered drug solution for needleless penetration of the treatment drug through the bladder wall into the diseased tissue. In one aspect, the delivery tip is shaped to be pressed against the bladder wall and deform the bladder wall without penetrating the wall. In this configuration, the delivery tip can comprise at least one graduated marker that can aligned with the bladder wall at the edge of the deformed area to provide an estimate of the relative depth of the delivery tip and the extent of the deformation. Each graduated marker can be positioned at a predetermined position to align the jet formed orifices with a particular tissue layer.

In another aspect, the delivery tip can further comprise a light projection system and at least one camera. In this configuration, the light projection system can be adapted to project a light beam against the bladder wall. The light beam can be configured provide a wavelength corresponding to the particular type of disorder to be treated so as to better identify the treatment site. The light projection system can be positioned to direct the light beam to approximate the point where each jet will strike the bladder wall. Similarly, each camera can be positioned to capture the light emitted from the light projection system. In one aspect, the bladder can be pre-treated with dye to further exaggerate the position of the diseased tissue.

A method of treating diseased tissue, according to an aspect of the present invention, comprises navigating a catheter having an integrated delivery tip through a urethra and into a bladder, wherein the delivery tip defines at least one orifice. The method further comprises pressing the delivery tip against the bladder wall to deform the bladder wall and align each orifice with a tissue layer of the bladder. The method also comprises feeding a treatment drug solution through the catheter and into the delivery tip. Finally, the method comprises forming at least one jet for penetrating the tissue layer into the targeted tissue. In one aspect, the method can also comprise projecting a light beam from the delivery tip having a wavelength corresponding to the diseased tissue in order to illuminate the diseased tissue.

The above summary of the various representative embodiments of the invention is not intended to describe each illustrated embodiment or every implementation of the invention.

Rather, the embodiments are chosen and described so that others skilled in the art can appreciate and understand the principles and practices of the invention. The figures in the detailed description that follow more particularly exemplify these embodiments.

BRIEF DESCRIPTION OF THE DRAWINGS

The invention can be completely understood in consideration of the following detailed description of various embodiments of the invention in connection with the accompanying drawings, in which.

Figure 1:
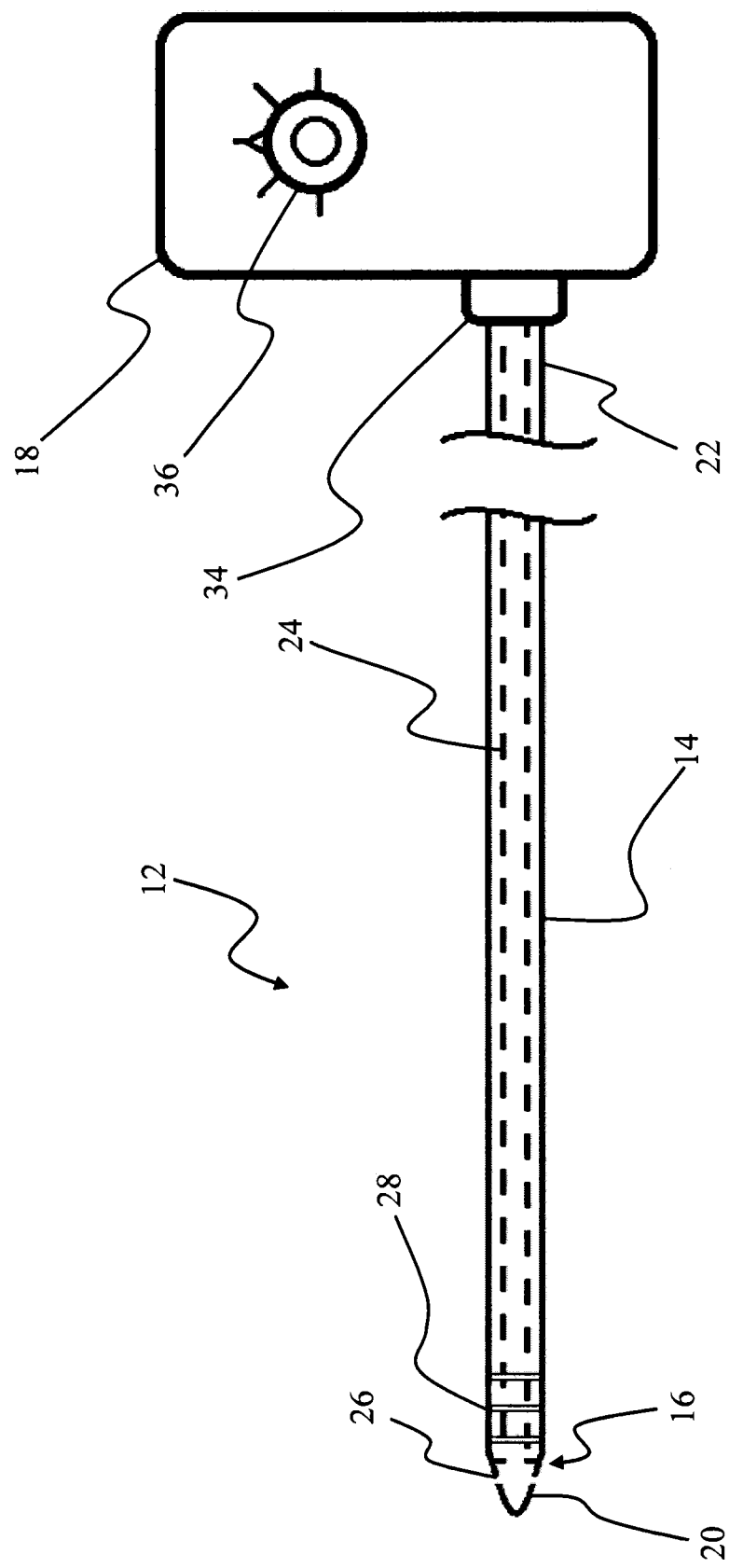
FIG. 1 is a partial cross-sectional view of a drug delivery system having a drug delivery tip for forming drug treatment solution jet according to an embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

As shown in FIG. 1, a drug delivery system 12, according to one aspect, comprises a catheter 14 having a delivery tip 16 and a control system 18. The catheter 14 further comprises a distal end 20 on which the delivery tip 16 is positioned and a proximal end 22 operably connected to the control system 18. The catheter 14 defines an internal lumen 24 for conveying a treatment drug solution from the control system 18 to the delivery tip 16. The delivery tip 16 further comprises at least one orifice 26 shaped to act as a jet nozzle forming a pressurized jet from the drug solution supplied by the control system 18. The orifices 26 are fabricated to resist expansion or change in shape that can affect the resulting pressure or shape of the jet formed. In one aspect, the treatment drug can be delivered to the delivery tip 16 at a high pressure. The pressure of the treatment drug can range from 2,000 psi to 5,000 psi in one aspect of the invention.

In one aspect, the catheter 14 and delivery tip 16 can comprise suitable high strength polymers including, for example, polyimide, polyetherimide available from General Electric under the trade name Ultem® and linear aromatic polymers such as PEEK™ available from Victrex PLC. In other aspects, the catheter 14 and delivery tip 16 can be reinforced by including materials such as nano-particles, clays and/or glass into the polymer blend.

Figure 2:
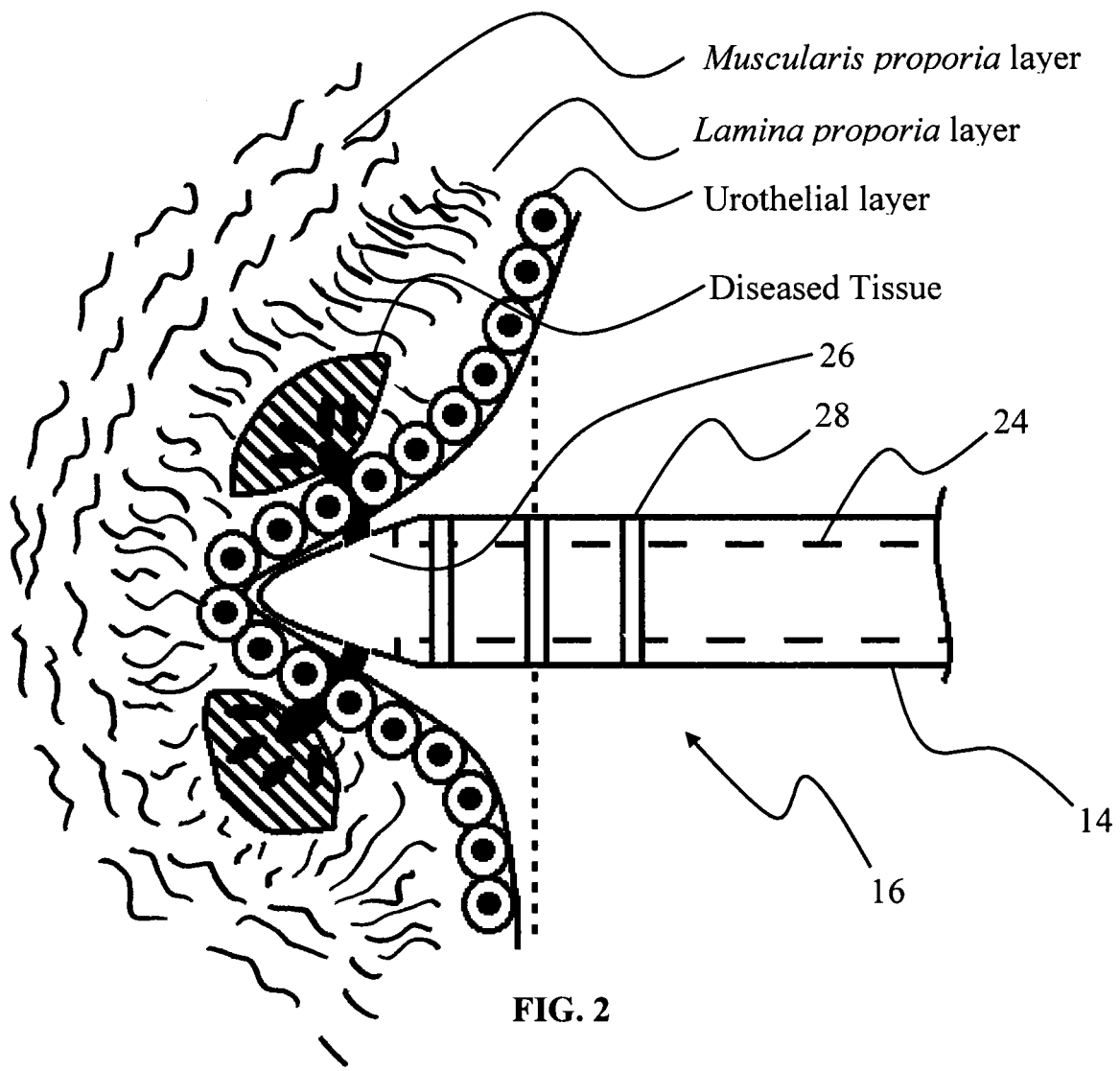
FIG. 2 is a representative schematic view of the drug delivery tip depicted in FIG. 1 illustrating delivering jets of treatment drug to diseased tissue according to an embodiment of the present invention.

As shown in FIGS. 1 to 2, in operation, the catheter 14 is navigated through the urethra and into the bladder until the delivery tip 16 is positioned proximate to the diseased tissue. The delivery tip 16 is positioned against the bladder wall and pushed into the bladder wall to deform the wall. In one aspect, the delivery tip 16 can be adapted to penetrate the bladder wall. The deformation of the bladder wall aligns the orifices with the different layers of the bladder wall. In one aspect, pressing the tip of the delivery tip 16 to a first depth aligns the orifices 26 with the urothelial layer such that the formed jets of treatment drug solution primarily enter the urothelial layer. Similarly, pressing the tip of the delivery tip 16 to a second depth aligns the orifices 26 with the lamina proporia layer of the bladder such that the formed jets of treatment drug solution primarily enter the lamina proporia layer. Also, pressing the tip of the delivery tip 16 to a third depth to align the orifices 26 with the detrusor or muscularis propria layer of the bladder. According to various aspects, the delivery tip 16 can be positioned at varying depths to align the orifices 26 with different tissue layers of the bladder wall.

As shown in FIGS. 1 to 2, the delivery tip 16 can further comprise a plurality of graduated markings 28 corresponding to predetermined depths for the delivery tip 16 within the bladder wall. In operation, the graduated markings 28 can be visually aligned with the portion of the bladder wall surrounding the deformed portion to provide a visual indicator of the alignment of the orifices 26 with the various bladder wall layers.

Figure 3:
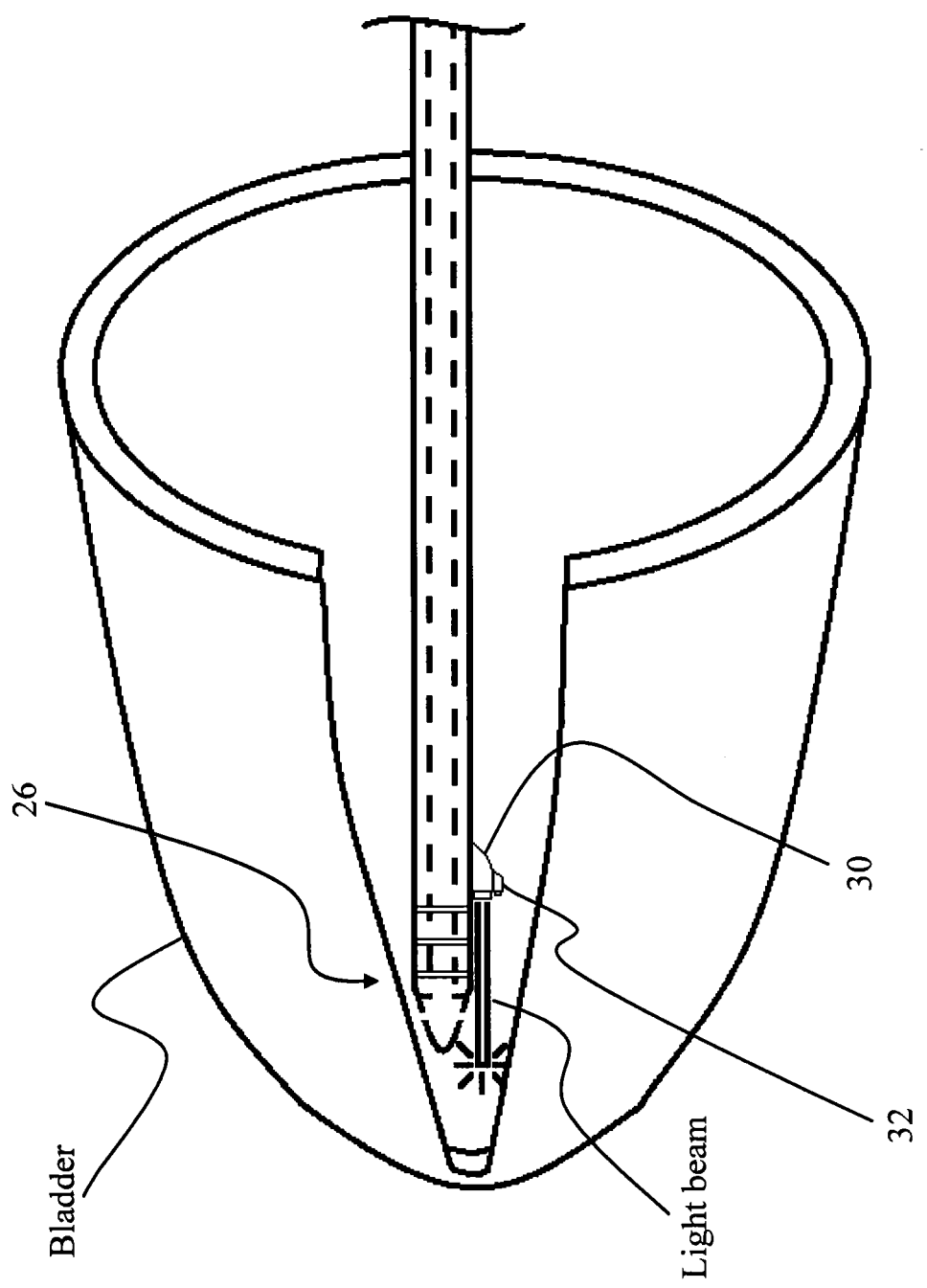
FIG. 3 is a representative schematic view of a drug delivery tip according to an embodiment of the present invention depicting illumination of diseased tissue for targeted delivery of treatment drugs.

As shown in FIG. 3, the delivery tip 16 can further comprise a light projection system 30 and at least one micro-camera 32. The light projection system 30 can provide a light beam having a wavelength corresponding to the particular type of disorder to be treated, thereby illuminating the diseased tissue and allowing for more accurate positioning of the delivery tip 16. The micro-camera 32 is used to identify the illuminated diseased tissue and align the delivery tip 16 for targeted delivery of the treatment drug. In one aspect, a dye can be first administered to further exaggerate the diseased tissue against the surrounding healthy tissue.

As shown in FIG. 1, in one aspect, the control system 18 can further comprise an adapter 34 for receiving the proximal end 22 of the catheter 14 to operably link the control system 18 with the delivery tip 16 via the catheter lumen 24. In one aspect, the control system 18 can comprise a manual control 36 for adjusting the relative pressure of the drug solution supplied to the delivery tip 16.

As shown in FIGS. 2-3, a method of treating diseased tissue within the bladder wall, according to an aspect of the present invention, comprises navigating the catheter 14 through the urethra and into the bladder. The method further comprises positioning the delivery tip 16 against the bladder wall and deforming the bladder wall by pressing the delivery tip 16 against the bladder wall to align the orifices 26 of the delivery tip 16 with the various layers of the bladder wall. Finally, the method comprises supplying a pressurized treatment drug solution through the catheter 14 to the delivery tip 16 such that the drug solution is formed into a plurality of jets for penetrating the bladder wall. In some embodiments, the method can further comprise providing a light projection system 30 proximate the delivery tip 16, wherein diseased tissue can be illuminated prior to treatment. The method can further comprise viewing the treatment site with a micro-camera 32.

While the invention is amenable to various modifications and alternative forms, specifics thereof have been shown by way of example in the drawings and described in detail. It is understood, however, that the intention is not to limit the invention to the particular embodiments described. On the contrary, the intention is to cover all modifications, equivalents, and alternatives falling within the spirit and scope of the invention as defined by the appended claims.

The invention claimed is:

1. A method of delivering drugs into a bladder wall, comprising:

advancing a needleless delivery tip on a catheter into proximity with a bladder wall;

illuminating the bladder wall with a light projection system having a wavelength corresponding to diseased tissue;

identifying the diseased tissue with a micro-camera; and delivering a treatment drug to the diseased tissue through an orifice in the needleless delivery tip.

2. The method of claim 1, further comprising: positioning the needleless delivery tip proximate the diseased tissue.

3. The method of claim 1, further comprising:

pushing the needleless delivery tip against the bladder wall such that the bladder wall deforms about the needleless delivery tip.

4. The method of claim 3, wherein the needleless delivery tip includes a plurality of graduated markers, wherein each graduated marker corresponds to a predetermined depth of the orifice with respect to the bladder wall, the method further comprising: aligning a selected graduated marker with the deformed bladder wall.

5. The method of claim 1, further comprising:

administering a dye to the bladder wall, wherein said dye is selected to promote visualization of the diseased tissue.

6. The method of claim 1, wherein delivery of the treatment drug further comprises:

pressurizing the treatment drug such that a pressurized jet of treatment drug is delivered through the orifice.

7. A method of delivering drugs into a bladder wall, comprising:

advancing a needleless delivery tip on a catheter into proximity with a bladder wall;

pushing the needleless delivery tip against the bladder wall such that the bladder wall deforms about the needleless delivery tip;

aligning a selected one of a plurality of graduated markers on the needleless delivery tip with the deformed bladder wall, wherein each of the plurality of graduated markers corresponds to a predetermined depth of the orifice with respect to the bladder wall; and delivering a treatment drug into the bladder wall through an orifice in the needleless delivery tip.

8. The method of claim 7, further comprising:

illuminating the bladder wall with a light projection system having a wavelength corresponding to diseased tissue; and identifying the diseased tissue with a micro-camera.

9. The method of claim 8, further comprising:

positioning the needleless delivery tip proximate the diseased tissue.

10. The method of claim 8, further comprising:

administering a dye to the bladder wall, wherein said dye is selected to promote visualization of the diseased tissue.

11. The method of claim 7, further comprising:

pressurizing the treatment drug such that a pressurized jet of treatment drug is delivered through the orifice.

12. A bladder treatment delivery system, comprising:

a delivery catheter having a needleless delivery tip, the needleless delivery tip including a delivery orifice, a light projection system and a micro camera, the light projection system adapted to provide a selected light wavelength, where said light wavelength corresponds to a type of diseased tissue on a bladder wall and said micro camera is adapted to image the light wavelength and identify the diseased tissue such that said delivery orifice can be positioned proximate the diseased tissue; and a control system for pressurizing a treatment fluid such that said treatment fluid flows through the delivery catheter and into the diseased tissue through the delivery orifice.

13. The bladder treatment delivery system of claim 12, wherein the needleless delivery tip includes a plurality of graduated markers, wherein each graduated marker corresponds to a predetermined depth of the delivery orifice with respect to the bladder wall.

14. The bladder treatment delivery system of claim 13, wherein the needleless delivery tip is pressed against the bladder wall to deform the bladder wall such that a selected one of the graduated markers is aligned with the deformed bladder wall for delivering the treatment fluid to the desired predetermined depth.

15. The bladder treatment delivery system of claim 12, further comprising:

a dye selected to promote visualization of the diseased tissue by the micro camera.

16. The bladder treatment delivery system of claim 12, wherein the control system comprises a manual control for adjusting the pressure of the treatment fluid supplied to the needleless delivery tip.

17. The bladder treatment delivery system of claim 12, wherein the delivery orifice is shaped to act as a jet nozzle.

18. A bladder treatment delivery system, comprising:

a delivery catheter having a needleless delivery tip including a delivery orifice, the needleless delivery tip including a plurality of graduated markers, each graduated marker corresponding to a predetermined depth of the delivery orifice with respect to a bladder wall; and a control system for pressurizing a treatment fluid such that said treatment fluid flows through the delivery catheter and is injected to diseased tissue on the bladder wall.

19. The bladder treatment delivery system of claim 18, wherein the needleless delivery tip includes a light projection system and a micro camera, the light projection system adapted to provide a selected light wavelength, where said light wavelength corresponds to the diseased tissue on the bladder wall and said micro camera is adapted to image the light wavelength and identify the diseased tissue such that said delivery orifice can be positioned proximate the diseased tissue.

20. The bladder treatment delivery system of claim 19, further comprising:

a dye selected to promote visualization of the diseased tissue by the micro camera.

21. The bladder treatment delivery system of claim 18, wherein the needleless delivery tip is pressed against the bladder wall to deform the bladder wall such that a selected one of the graduated markers is aligned with the deformed bladder wall for delivering the treatment fluid to the desired predetermined depth.

22. The bladder treatment delivery system of claim 18, wherein the control system comprises a manual control for adjusting the pressure of the treatment fluid supplied to the needleless delivery tip.

23. The bladder treatment delivery system of claim 18, wherein the delivery orifice is shaped to act as a jet nozzle.

* * * * *